(12) United States Patent
Kawai et al.

(10) Patent No.: US 11,027,604 B2
(45) Date of Patent: Jun. 8, 2021

(54) HYDROGEN DETECTION APPARATUS, FUEL CELL VEHICLE, HYDROGEN LEAK MONITORING SYSTEM, COMPOUND SENSOR MODULE, HYDROGEN DETECTION METHOD, AND RECORDING MEDIUM

(71) Applicant: Panasonic Intellectual Property Management Co., Ltd., Osaka (JP)

(72) Inventors: Ken Kawai, Osaka (JP); Shinichi Yoneda, Kyoto (JP)

(73) Assignee: PANASONIC SEMICONDUCTOR SOLUTIONS CO., LTD., Kyoto (JP)

( * ) Notice: Subject to any disclaimer, the term of this patent is extended or adjusted under 35 U.S.C. 154(b) by 90 days.

(21) Appl. No.: 16/468,558

(22) PCT Filed: Dec. 8, 2017

(86) PCT No.: PCT/JP2017/044108
§ 371 (c)(1),
(2) Date: Jun. 11, 2019

(87) PCT Pub. No.: WO2018/110441
PCT Pub. Date: Jun. 21, 2018

(65) Prior Publication Data
US 2020/0083549 A1 Mar. 12, 2020

Related U.S. Application Data

(60) Provisional application No. 62/434,686, filed on Dec. 15, 2016.

(51) Int. Cl.
*G01N 33/00* (2006.01)
*B60K 1/04* (2019.01)
(Continued)

(52) U.S. Cl.
CPC .............. *B60K 1/04* (2013.01); *B60L 3/0053* (2013.01); *G01M 3/16* (2013.01); *G01N 27/12* (2013.01);
(Continued)

(58) Field of Classification Search
CPC .......... B60K 1/04; B60L 3/0053; G01M 3/16; G01N 27/12; G01N 33/005; H01M 8/04298
See application file for complete search history.

(56) References Cited

U.S. PATENT DOCUMENTS 4,399,424 A * 8/1983 Rigby ..................... G01N 27/12
338/308
5,321,146 A * 6/1994 Royster, Jr. ........... C07F 11/005
556/57
(Continued)

FOREIGN PATENT DOCUMENTS

JP 11-66464 3/1999
JP 2004-139842 5/2004
(Continued)

OTHER PUBLICATIONS

Yu et al., Hydrogen gas sensing properties of Pt/Ta2O5 Schottky diodes based on Si and SiC substrates (Year: 2011).*
(Continued)

*Primary Examiner* — Patrick Assouad
*Assistant Examiner* — Demetrius R Pretlow
(74) *Attorney, Agent, or Firm* — Wenderoth, Lind & Ponack, L.L.P.

(57) ABSTRACT

A hydrogen detection apparatus includes a hydrogen sensor, a sensor control circuit configured to sense a resistance value of the hydrogen sensor, and a microcomputer configured to set an off time that differs depending on an operating environment and intermittently drive the sensor control
(Continued)

circuit. The hydrogen sensor includes a first electrode; a metal-oxide layer on the first electrode, and in which a resistance value is configured to change in response to contacting hydrogen atoms; a second electrode on the metal-oxide layer; and an insulating film that covers at least a portion of lateral surfaces of the first electrode, the metal-oxide layer, and the second electrode. A portion of at least one of: (i) a first interface between the first electrode and the metal-oxide layer; and (ii) a second interface between the second electrode and the metal-oxide layer is uncovered by the insulating film and exposed to a detection space.

14 Claims, 7 Drawing Sheets

(51) Int. Cl.
*B60L 3/00* (2019.01)
*G01M 3/16* (2006.01)
*G01N 27/12* (2006.01)
*H01M 8/04298* (2016.01)
*B60L 50/71* (2019.01)

(52) U.S. Cl.
CPC ...... *G01N 33/005* (2013.01); *H01M 8/04298* (2013.01); *B60L 50/71* (2019.02); *B60Y 2200/91* (2013.01); *B60Y 2400/202* (2013.01)

(56) References Cited

U.S. PATENT DOCUMENTS

| | | | | |
|---|---|---|---|---|
| 5,428,988 | A * | 7/1995 | Starkovich | G01M 3/16 73/40 |
| 6,012,327 | A * | 1/2000 | Seth | G01N 27/125 422/90 |
| 6,401,465 | B1 * | 6/2002 | Meinzer | G01M 3/228 62/129 |
| 2001/0003916 | A1 * | 6/2001 | Nomura | G01N 33/0047 73/31.06 |
| 2002/0187075 | A1 * | 12/2002 | Nadanami | G01N 33/005 422/98 |
| 2003/0024813 | A1 * | 2/2003 | Taniguchi | G01N 33/005 204/424 |
| 2004/0099047 | A1 * | 5/2004 | Raisanen | G01N 27/12 73/25.05 |
| 2005/0258051 | A1 * | 11/2005 | Ono | G01N 33/005 205/775 |
| 2006/0065526 | A1 * | 3/2006 | Ono | G01N 27/4071 204/426 |
| 2006/0114114 | A1 * | 6/2006 | Nakano | G08B 25/08 340/632 |
| 2006/0263255 | A1 * | 11/2006 | Han | B82Y 30/00 422/83 |
| 2007/0052516 | A1 * | 3/2007 | Hines | B82Y 15/00 338/34 |
| 2007/0209937 | A1 * | 9/2007 | Hoagland | G01N 33/0073 204/424 |
| 2009/0035612 | A1 * | 2/2009 | Suematsu | H01M 8/04089 429/432 |
| 2009/0064764 | A1 * | 3/2009 | Kizaki | B60L 58/33 73/40.5 R |
| 2009/0188316 | A1 * | 7/2009 | Erdler | G01N 27/12 73/335.05 |
| 2010/0012919 | A1 * | 1/2010 | Park | G01N 27/12 257/9 |
| 2010/0269569 | A1 * | 10/2010 | Yang | G01N 27/127 73/31.06 |
| 2011/0088456 | A1 * | 4/2011 | Ren | H01L 29/42316 73/31.06 |
| 2012/0237843 | A1 * | 9/2012 | Paganelli | H01M 8/2483 429/429 |
| 2012/0242170 | A1 | 9/2012 | Kuwano et al. | |
| 2012/0291522 | A1 * | 11/2012 | Tsukabayashi | H01M 8/04097 73/23.21 |
| 2014/0290338 | A1 * | 10/2014 | Kim | G01N 27/414 73/31.06 |
| 2014/0356971 | A1 * | 12/2014 | Kozlow | G01N 33/0044 436/121 |
| 2015/0171437 | A1 * | 6/2015 | Kongkanand | G01N 33/005 429/490 |
| 2016/0103082 | A1 * | 4/2016 | Kimura | G01N 33/005 73/25.01 |
| 2018/0079309 | A1 * | 3/2018 | Ban | H01M 8/04664 |
| 2019/0100851 | A1 * | 4/2019 | Choa | C25D 7/123 |

FOREIGN PATENT DOCUMENTS

| | | |
|---|---|---|
| JP | 2004-158340 | 6/2004 |
| JP | 2006-118939 | 5/2006 |
| JP | 2006-157248 | 6/2006 |
| JP | 2007-256072 | 10/2007 |
| JP | 2013-165422 | 8/2013 |

OTHER PUBLICATIONS

Song et al., AlGaN/GaN Schottky diode hydrogen sensor performance at high temperatures with different catalytic metals (Year: 2005).*

International Search Report (ISR) dated Mar. 6, 2018 in International (PCT) Application No. PCT/JP2017/044108.

* cited by examiner

| STATE | $t_{off}$ |
|---|---|
| $Q_1$ | $t_1$ |
| $Q_2$ | $t_2$ |
| $Q_3$ | $t_3$ |
| ⋮ | ⋮ |

| STATE | $t_{off}$ |
|---|---|
| PARKED | $t_1 (> t_3)$ |
| STOPPED | $t_2 (> t_3)$ |
| TRAVELING | $t_3$ |

| STATE | $t_{off}$ |
|---|---|
| PARKED (OPEN SPACE) | $t_{1a} (> t_{1b})$ |
| PARKED (ENCLOSED SPACE) | $t_{1b} (> t_3)$ |
| STOPPED | $t_2 (> t_3)$ |
| TRAVELING | $t_3$ |

| STATE | $t_{off}$ |
|---|---|
| NORMAL | $t_4$ |
| CAUTION | $t_5 \, (< t_4)$ |
| MALFUNCTION (SUBMERSION) | SUSPEND HYDROGEN SENSING |

US 11,027,604 B2

HYDROGEN DETECTION APPARATUS, FUEL CELL VEHICLE, HYDROGEN LEAK MONITORING SYSTEM, COMPOUND SENSOR MODULE, HYDROGEN DETECTION METHOD, AND RECORDING MEDIUM

TECHNICAL FIELD

The present disclosure relates to a hydrogen detection apparatus, fuel cell vehicle, hydrogen leak monitoring system, compound sensor module, hydrogen detection method, and recording medium.

BACKGROUND ART

Patent Literature (PTL) 1 discloses a circuit apparatus that includes an amplifier circuit to which a signal is input from a sensor and a control circuit, the circuit apparatus causing the sensor and the amplifier circuit to intermittently operate via the control circuit.

PTL 2 discloses a gas leak warning device that performs a purge process for removing miscellaneous gases, dust, and the like adsorbed and adhered to a gas sensor due to intermittently heating up the gas sensor to a temperature above the usage temperature.

Adopting the point of view of PTL 1 in PTL 2, a gas detection process may also be performed intermittently along with the purge process. With this, the gas leak warning device is expected to save more energy.

CITATION LIST

Patent Literature

PTL 1: Japanese Unexamined Patent Application Publication No. 2013-165422.
PTL 2: Japanese Unexamined Patent Application Publication No. 11-66464.

SUMMARY OF THE INVENTION

Technical Problems

The inventors have studied a hydrogen detection apparatus for detecting hydrogen gas. A hydrogen detection apparatus that enables on-board and infrastructure equipment to save energy together with reliably ensuring the safety of a fuel cell vehicle is desirable since failure to detect the hydrogen gas may be linked to grave accidents.

Accordingly, the present disclosure aims to provide a hydrogen detection apparatus capable of optimizing a trade-off between ensuring the safety of the fuel cell vehicle and saving energy.

Solution to Problems

A hydrogen detection apparatus according to an aspect of the present disclosure includes a hydrogen sensor in which a resistance value fluctuates in response to a presence of a hydrogen gas, a sensor control circuit that senses the resistance value of the hydrogen sensor, and a microcomputer that sets an off time that differs depending on an operating environment and intermittently drives the sensor control circuit. The hydrogen sensor includes a first electrode; a metal-oxide layer that is disposed on the first electrode, and in which a resistance value changes in response to contacting hydrogen atoms; a second electrode disposed on the metal-oxide layer; and an insulating film that covers at least a portion of lateral surfaces of the first electrode, the metal-oxide layer, and the second electrode. A portion of at least one of (i) a first interface between the first electrode and the metal-oxide layer and (ii) a second interface between the second electrode and the metal-oxide layer is uncovered by the insulating film and exposed to a detection space.

Advantageous Effect of Invention

A hydrogen detection apparatus according to an aspect of the present disclosure makes it possible to set an off time that differs depending on an operating environment and intermittently monitor for hydrogen leaks. This makes it possible to, for example, attain a hydrogen detection apparatus that is capable of optimizing a trade-off between ensuring the safety of the fuel vehicle and saving energy since operations such as shortening an off time and frequently monitoring for hydrogen leaks become possible in environments where reliability is emphasized compared to environments where energy saving is emphasized.

DESCRIPTION OF EXEMPLARY EMBODIMENTS

Figure 1:
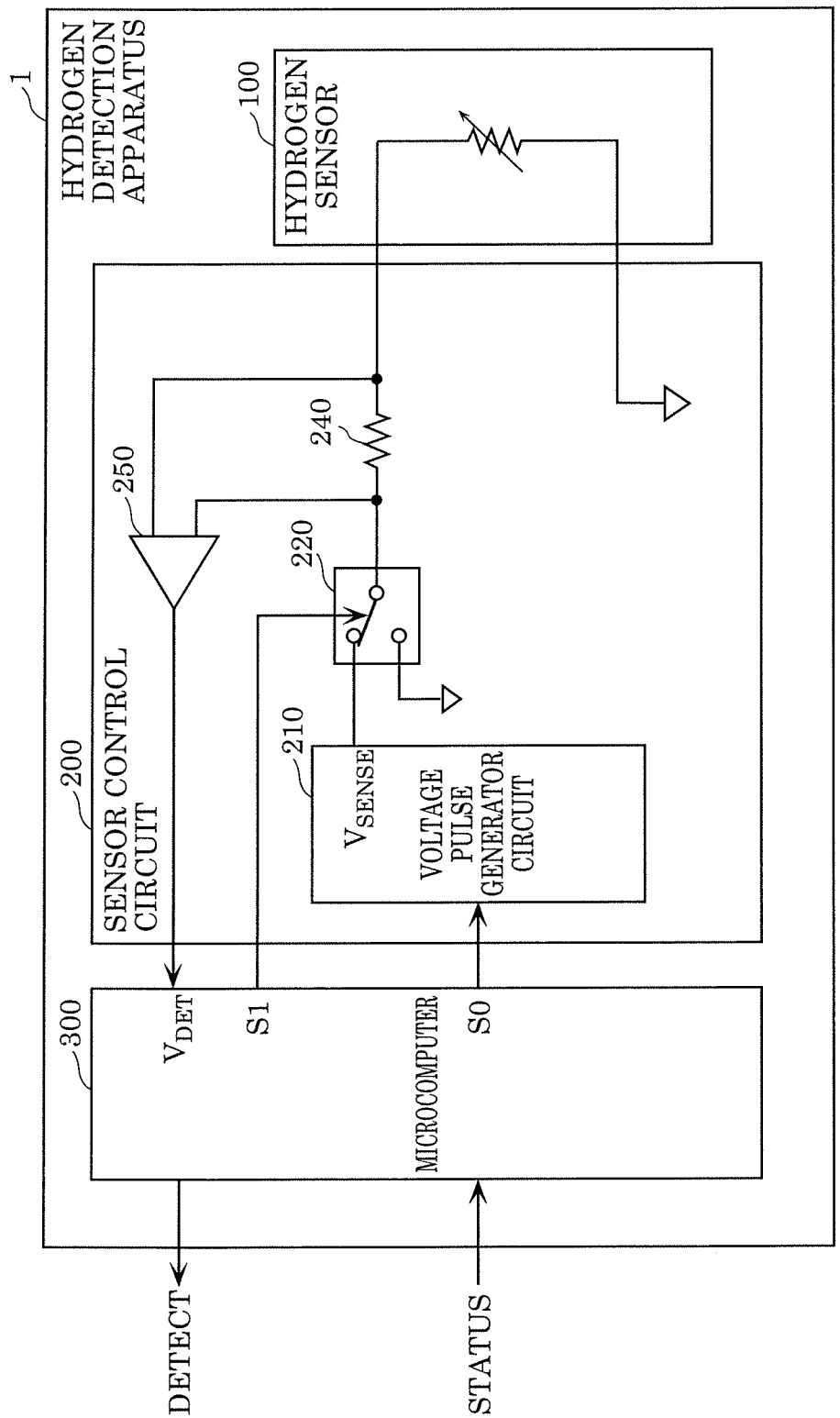
FIG. 1 is a function block diagram showing an example of a configuration of a hydrogen detection apparatus according to Embodiment 1.

Underlying Knowledge Forming Basis of Present Disclosure

Causing a hydrogen detection apparatus to intermittently operate is useful for saving energy. There are instances, however, where merely causing the hydrogen detection apparatus to intermittently operate does not attain the necessary reliability or save enough energy.

For example, contributing factors affecting the safety of the hydrogen detection apparatus, e.g. an occurrence probability of hydrogen gas actually leaking from the equipment and how easy it is to refill the hydrogen gas in the event the hydrogen gas has leaked, greatly differ in accordance with and operating state of the equipment and installation environment.

Thus, the inventors believe that, depending on the environment, the safety of a fuel cell vehicle cannot be sufficiently ensured due to delays in the detection, or that the detection is performed too frequently when causing the hydrogen detection apparatus to be intermittently operated with a fixed frequency, i.e., with a fixed off time, which impairs the ability to save energy.

The inventors propose a hydrogen detection apparatus that sets an off time that differs depending on an operating environment, and that intermittently performs a hydrogen detection in order to solve such a problem.

Hereinafter, embodiments in the present disclosure will be described with reference to the drawings.

Note that, in each drawing, components representing configurations, operations, and effects that are substantially the same as components described previous thereto have the same reference numerals and descriptions are omitted. Numerical values, materials, components, compositions, shapes, deposition methods, connection relationships of the components, and the like mentioned below are mere examples for concretely describing the embodiments in the present disclosure and are not intended to limit the present disclosure. Components in the following embodiments not mentioned in any of the independent claims that define the broadest concepts are described as optional elements.

Embodiment 1

(Configuration of Hydrogen Detection Apparatus)

FIG. 1 is a function block diagram showing an example of a configuration of a hydrogen detection apparatus according to Embodiment 1. As illustrated in FIG. 1, hydrogen detection apparatus 1 includes hydrogen sensor 100, sensor control circuit 200, and microcomputer 300.

Hydrogen sensor 100 is a sensor in which a resistance value fluctuates in accordance with a presence of hydrogen gas. Hydrogen sensor 100 is an example not limited to the foregoing and may also include a resistive element using a reduction reaction by the hydrogen gas of the metal oxide. In such a resistive element, the hydrogen gas can be detected by decreasing the resistance value that is produced when the metal oxide metalizes due to the reduction reaction. A concrete configuration example of hydrogen sensor 100 will be described later.

Sensor control circuit 200 is an electric circuit for controlling hydrogen sensor 100, and includes voltage pulse generator circuit 210, switch 220, resistor 240, and amplifier 250.

Voltage pulse generator circuit 210 outputs a pulse sensing voltage $V_{SENSE}$ in accordance with control signal S0. Sensing voltage $V_{SENSE}$ is used for sensing the resistance value of hydrogen sensor 100 of which one example is a voltage of approximately 0.8 V to 1.0 V.

Switch 220 is switched in accordance with control signal S1 so that sensing voltage $V_{SENSE}$ is applied to hydrogen sensor 100.

Resistor 240 and amplifier 250 output detection voltage $V_{DET}$ representing a sensing current (i.e., the resistance value of hydrogen sensor 100) that flows in hydrogen sensor 100 when sensing voltage $V_{SENSE}$ is applied to hydrogen sensor 100.

Microcomputer 300 sets an off time that differs depending on an operating environment of hydrogen detection apparatus 1, and intermittently drives sensor control circuit 200. Microcomputer 300 includes a processor, memory, and input/output port (not illustrated), and may also intermittently drive sensor control circuit 200 due to the microcomputer executing a computer program prestored in the memory.

The operating environment of hydrogen detection apparatus 1 may also refer to an operating state of a target apparatus or target equipment that performs the hydrogen detection (hereinafter, also referred to as monitoring target). As an example that is not limited, hydrogen detection apparatus 1 is installed in the fuel cell vehicle, and the traveling, stopped, and parked states of the fuel cell vehicle correspond to the operating environment of hydrogen detection apparatus 1.

Microcomputer 300 intermittently drives sensor control circuit 200 by issuing control signals S0 and S1 in accordance with state signal STATUS indicating the operating environment of hydrogen detection apparatus 1. Microcomputer 300 outputs detection signal DETECT indicating that hydrogen gas has been detected based on detection voltage $V_{DET}$ obtained from sensor control circuit 200.

(Operation of Hydrogen Detection Apparatus)

Figures 2, 3:
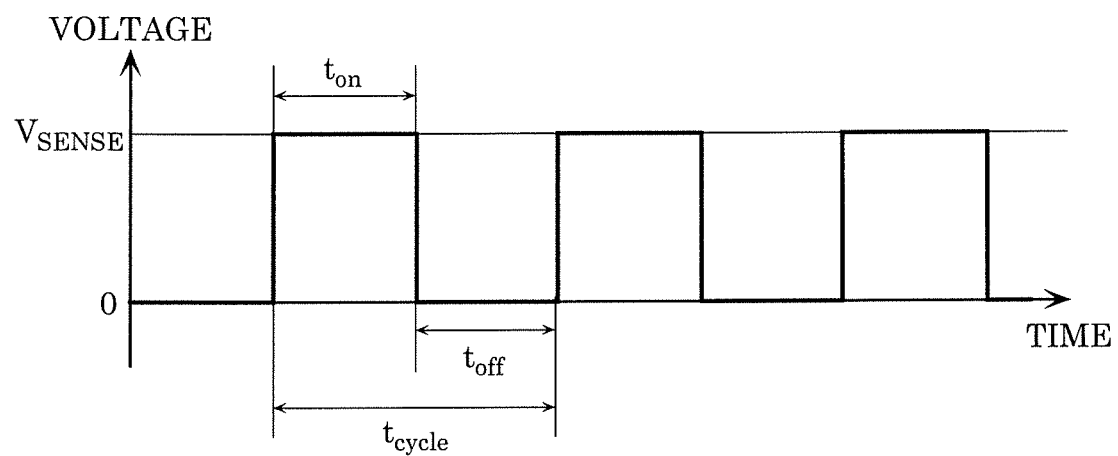
FIG. 2 is a timing diagram of an example of a hydrogen detection operation according to Embodiment 1.
FIG. 3 is a diagram showing an example of an off time table according to Embodiment 1.

FIG. 2 is a timing diagram of an example of a hydrogen detection operation performed under a control of microcomputer 300. Timing diagram in FIG. 2 shows an example of a temporal waveform of the voltage applied to hydrogen sensor 100. As illustrated in FIG. 2, a cycle of the intermittent operation includes a sensing period with a duration of on time $t_{on}$ and an idle period with a duration of off time $t_{off}$.

In the sensing period, sensing voltage $V_{SENSE}$ is applied to hydrogen sensor 100, and the resistance value of hydrogen sensor 100 is measured. In the idle period, the operation of sensor control circuit 200 is suspended, and the power consumption of hydrogen detection apparatus 1 is limited to a minimum.

On time $t_{on}$ is a time duration hydrogen sensor 100 needs to detect hydrogen gas after sensing voltage $V_{SENSE}$ has started being applied, and, to give one example, a time is set ranging between approximately one second and one minute. On time $t_{on}$ may also be a fixed time duration. Off time $t_{off}$ is a time duration during which a monitoring frequency necessary for ensuring the safety of fuel cell vehicle 800 can be attained, and differs depending on the operating environment of hydrogen detection apparatus 1.

Microcomputer 300 may prestore the off time $t_{off}$ used in each operating environment.

FIG. 3 is a diagram showing an example of an off time table that stores an off time of each operating environment. Off time table 310 is included in the memory of microcomputer 300. Off time table 310 contains, per entry, states Q1, Q2, Q3 . . . of the monitoring target, and times t1, t2, t3 . . . used as off time $t_{off}$ in the corresponding states.

The hydrogen detection operation in hydrogen detection apparatus 1 will be described in detail.

Figure 4:
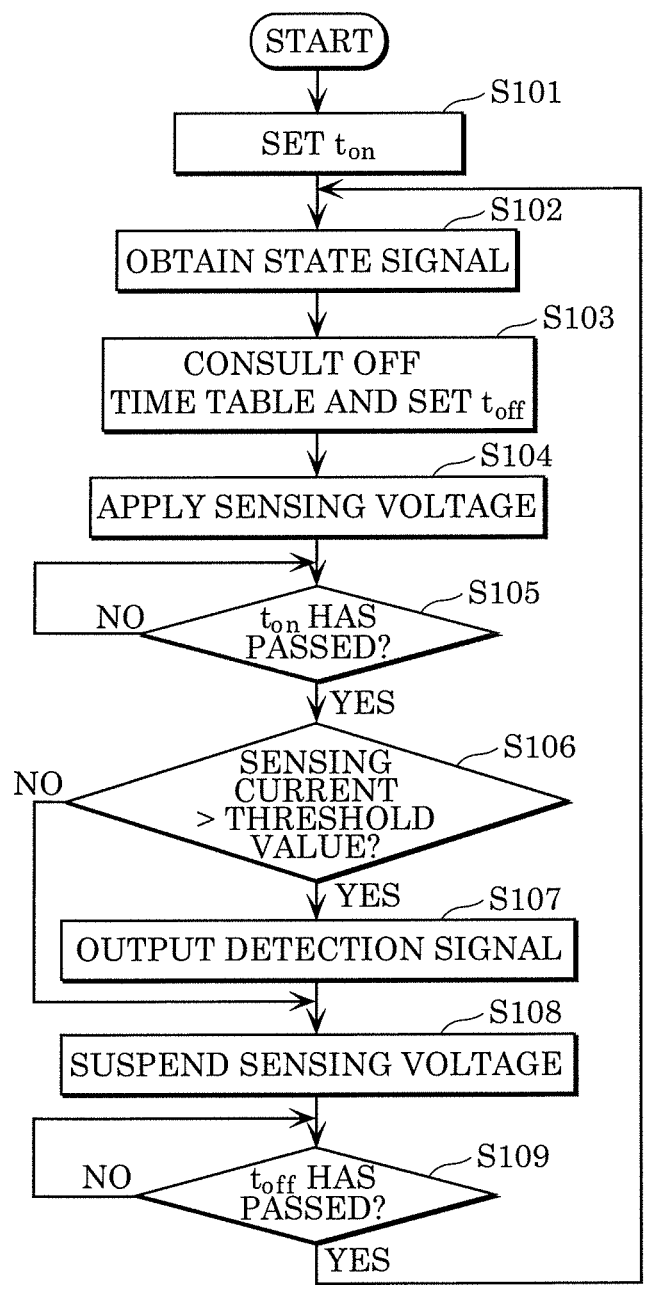
FIG. 4 is a flowchart of a detailed example of the hydrogen detection operation according to Embodiment 1.

FIG. 4 is a flowchart of a detailed example of the hydrogen detection operation. FIG. 4 mainly shows in detail an operation with microcomputer 300 as the main subject.

On time $t_{on}$ is first set in microcomputer 300 (S101). On time $t_{on}$ may also be set at a suitable fixed duration in accordance with hydrogen sensor 100.

Microcomputer 300 next obtains state signal STATUS (S102). Off time table 310 is consulted, and off time $t_{off}$ is set corresponding to the state represented by state signal STATUS (S103).

Microcomputer 300 next issues control signals S0 and S1 during on time $t_{on}$, and sensor control circuit 200 applies sensing voltage $V_{SENSE}$ to hydrogen sensor 100 in accordance with control signals S0 and S1 (S104, S105).

When the sensing current represented by detection voltage $V_{DET}$ exceeds a preset threshold value while sensing voltage $V_{SENSE}$ is being applied (YES in S106), microcomputer 300 outputs detection signal DETECT indicating that hydrogen gas has been detected (S107).

After on time $t_{on}$ has passed, microcomputer 300 suspends control signal S0 until off time $t_{off}$ has passed, and sensor control circuit 200 stops applying sensing voltage $V_{SENSE}$ to hydrogen sensor 100 in accordance with the suspension of control signal S0 (S108, S109). In the meantime, power supply to amplifier 250 and a clock of microcomputer 300 may be suspended, and the power consumption of hydrogen detection apparatus 1 may be limited to a minimum.

After off time $t_{off}$ has passed, subsequent operation of the cycle repeats from step S102.

As described above, hydrogen detection apparatus 1 makes it possible to set the off time that differs depending on the operating environment, and to intermittently perform the hydrogen detection. This makes it possible, for example, to optimize the trade-off between ensuring the safety of the fuel cell vehicle and saving energy since operations such as shortening an off time and frequently performing the hydrogen detection become possible in environments where there is a high risk of hydrogen leaks compared to environments where there is a low risk of hydrogen leaks.

Embodiment 2

(Configuration of Hydrogen Sensor)

A gas sensor that can be used as hydrogen sensor 100 of hydrogen detection apparatus 1 described in Embodiment 1 will be described in Embodiment 2. The gas sensor has been conceived by the inventors, and is filed as a related patent in Japanese Patent Application No. 2017-169614 (undisclosed at time of application of the present application). The main section of the specification of the related patent at time of application is cited in the description of Embodiment 2.

The gas sensor according to Embodiment 2 has a structure in which electrode layers are laminated on and under the metal-oxide layer as its basis. The gas sensor passes through at least a portion of the electrode layer on top of the metal-oxide layer, is formed so that an interface thereof with the electrode layer on top of the metal-oxide layer is exposed, and can detect gas including hydrogen without having to heat up the gas with a heater. Gas including hydrogen here is a general term for any gas including molecules with hydrogen atoms, and, to give an example, can include hydrogen, methane, alcohol, and the like.

Figure 5A:
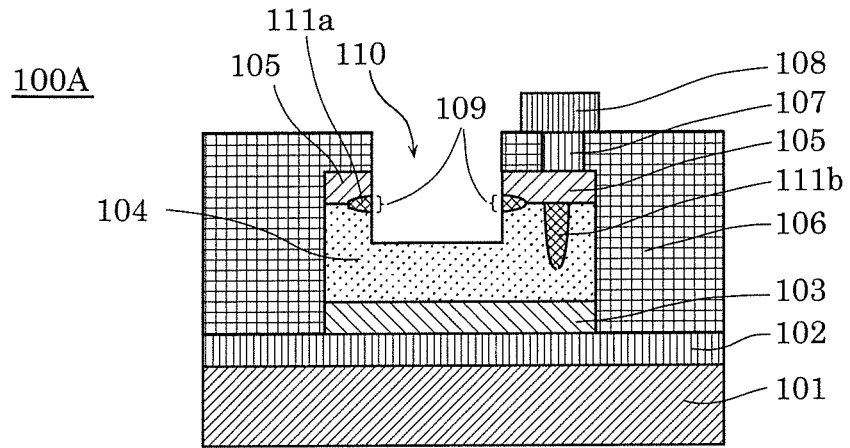
FIG. 5A is a cross-sectional view of an example of a structure of a hydrogen sensor according to Embodiment 2.
Figure 5B:
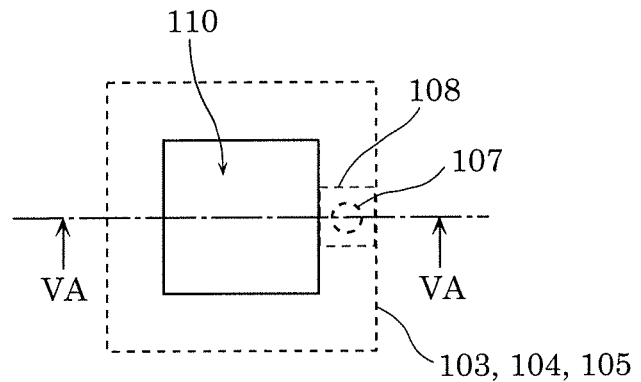
FIG. 5B is a plan view of the example of the structure of the hydrogen sensor according to Embodiment 2.

FIG. 5A is a cross-sectional view of a configuration example of gas sensor 100A according to Embodiment 2. FIG. 5B is a plan view of gas sensor 100A according to Embodiment 2. The cross-section in FIG. 5A corresponds to a cross-section line VA-VA in FIG. 5B seen along the arrows.

Gas sensor 100A includes substrate 101, insulating film 102 formed on substrate 101, first electrode 103 formed on insulating film 102, second electrode 105, metal-oxide layer 104 interposed between first electrode 103 and second electrode 105, insulating film 106, via 107, and wiring conductor 108.

Metal-oxide layer 104 is disposed between first electrode 103 and second electrode 105. Metal-oxide layer 104 transitions reversibly between a high-resistance state and a low-resistance state in accordance with (i) a voltage applied between first electrode 103 and second electrode 105 (ii) and a presence of gas including hydrogen within the gas that second electrode 105 contacts.

Insulating film 106 is penetrated by via 107 and connected to second electrode 105 in a portion that covers an upper surface of second electrode 105. Wiring conductor 108 is disposed above via 107.

Aperture 110 further passes through insulating film 106 and at least a portion of second electrode 105. As illustrated in FIG. 5B, aperture 110 is a rectangular cavity disposed at a position including center of gas sensor 100A in a plan view. As illustrated in FIG. 5A, insulating film 106 is disposed around aperture 110. Note that aperture 110 may also be disposed in a position that does not include the center of gas sensor 100A in the plan view, and need not be rectangular. Interface 109 where second electrode 105 and metal-oxide layer 104 contact each other is exposed so that interface 109 comes into contact with gas including hydrogen, which is an inspection target. Interface 109 is a first interface.

Figure 5C:
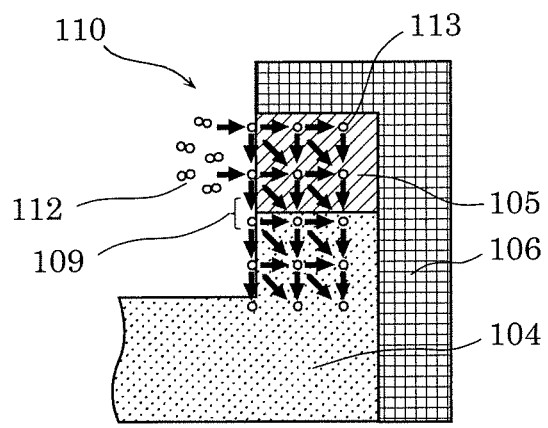
FIG. 5C is an enlarged cross-sectional view of a main section of a hydrogen sensor according to Embodiment 2.

When second electrode 105 includes a metal containing a catalytic action (e.g. platinum (Pt)), gas molecules 112 of gas including hydrogen dissociate from hydrogen atoms 113 at an exposed surface of second electrode 105 on a lateral surface of aperture 110, as illustrated in FIG. 5C. Since lateral surfaces of second electrode 105 and metal-oxide layer 104 are exposed due to aperture 110, hydrogen atoms 113 that are dissociated on a lateral surface of second electrode 105 easily diffuse from the surface of second electrode 105 to the lateral surface of metal-oxide layer 104, a new dissociation reaction occurs more easily at the lateral surface of second electrode 105, and more hydrogen atoms 113 are generated. These hydrogen atoms 113 diffuse from the surface of second electrode 105 or metal-oxide layer 104 to an interior thereof, and a reduction reaction occurs inside metal-oxide layer 104.

When metal-oxide layer 104 is an oxygen (O)-deficient metal oxide, metal-oxide layer 104 reacts more easily with hydrogen atoms and the like because metal-oxide layer 104 is chemically unstable, and the reaction with hydrogen atoms can be expected to be facilitated.

Note that in the present disclosure, "oxygen deficient degree" of the metal oxide refers to a ratio of an oxygen deficiency amount in the metal oxide to an amount of oxygen in the metal oxide and a stoichiometric compositional metal oxide made up of the same chemical elements. Note that the oxygen deficiency amount is the amount of oxygen in the metal oxide subtracted from the amount of oxygen in the stoichiometric compositional metal oxide. When it is possible there is a plurality of stoichiometric compositional metal oxides being made up of the same chemical elements as the metal oxide, the oxygen deficiency degree of the metal oxide is defined based on one of the plurality of stoichiometric composition metal oxides having the highest resistance value. The stoichiometric compositional metal oxide is more stable and has a higher resistance value than a metal oxide with another composition.

For example, when the metal is tantalum (Ta), the stoichiometric compositional oxide according to the above-mentioned definition can be expressed with $TaO_{2.5}$ since a composition thereof is $Ta_2O_5$. The oxygen deficiency degree of $TaO_{2.5}$ is 0% and the oxygen deficiency degree of $TaO_{1.5}$ is $(2.5-1.5)/2.5=40\%$. A metal oxide with too much oxygen has a negative oxygen deficiency degree. Note that in the present specification, the oxygen deficiency degree is described as including a positive value, 0, and negative value, provided the present specification is not rejected.

A metal oxide with a low oxygen deficiency degree has a high resistance value since the metal oxide is closer to a stoichiometric compositional metal oxide, and a metal oxide with a high oxygen deficiency degree has a low resistance value since the metal oxide is closer to a metal that is a component of the metal oxide. Since the dissociation reaction to the hydrogen atoms occurs at second electrode 105, the dissociation reaction can be said to occur the most easily proximate to interface 109 between second electrode 105 and metal-oxide layer 104.

Gas sensor 100A may include oxygen-deficient region 111a inside metal-oxide layer 104 that contacts second electrode 105. Oxygen-deficient region 111a occurs, for example, due to etching damage sustained by metal-oxide layer 104 when forming aperture 110 or second electrode 105. Oxygen-deficient region 111a may also amorphize by mixing second electrode 105 and metal-oxide layer 104 proximate to the interface between second electrode 105 and metal-oxide layer 104. Oxygen-deficient region 111a is formed at an exposed portion that contacts gas including hydrogen or proximate to interface 109 between second electrode 105 and metal-oxide layer 104.

Gas sensor 100A may also include local region 111b inside metal-oxide layer 104. Local region 111b is formed due to electrical breakdown of a portion of metal-oxide layer 104 by applying a voltage between first electrode 103 and second electrode 105. The electrical breakdown portion of metal-oxide layer 104 has a local shortage of oxygen, and is in a state in which current flows easily. In other words, local region 111b includes an oxygen-deficient, microscopic conductive path (filament) due to the electrical breakdown. The oxygen deficiency degree in local region 111b is higher than the oxygen deficiency degree around local region 111b (i.e., a bulk region of metal-oxide layer 104).

In gas sensor 100A including local region 111b, the current inside metal-oxide layer 104 flows to local region 111b in a concentrated manner when the voltage is applied between first electrode 103 and second electrode 105. This configuration enables, gas sensor 100A, second electrode 105 to be heated up due to the generation of heat in local region 111b, and perform the dissociation to the hydrogen atoms and the reduction reaction of the metal oxide in local region 111b.

The filament including local region 111b may be formed in only one place in metal-oxide layer 104 of gas sensor 100A, but a plurality of filaments may also be strewn throughout metal-oxide layer 104. The number of filaments can be confirmed through, for example, Electron Beam Absorbed Current (EBAC) analysis.

In this manner, gas sensor 100A is characterized by the resistance value between first electrode 103 and second electrode 105 fluctuating when second electrode 105 contacts gas including hydrogen. With this characteristic, gas sensor 100A can detect gas including hydrogen by detecting a reduction in the resistance value between first electrode 103 and second electrode 105 when the gas that is the inspection target contacts gas sensor 100A.

Hereinafter, the configuration of gas sensor 100A for obtaining reaction characteristics with respect to stable hydrogen will be described in more detail.

Metal-oxide layer 104 contains an oxide including one of three metals to be selected from a metal that can take on a plurality of oxidation states beginning as a transition metal, tin (Sn), and aluminum (Al). A host metal of the metal oxide may also be selected from at least one of (i) a transition metal e.g. Ta, hafnium (Hf), titanium (Ti), zirconium (Zr), niobium (Nb), tungsten (W), nickel (Ni), iron (Fe), chromium (Cr), cobalt (Co), manganese (Mn), vanadium (V), cerium (Ce), and copper (Cu), (ii) Sn, and (iii) aluminum (Al).

Metal-oxide layer 104 may also be an oxygen-deficient metal oxide with a lower oxygen composition ratio than the stoichiometric compositional metal oxide. The stoichiometric compositional metal oxide is a typical insulator, whereas the oxygen-deficient metal oxide is characterized by having an oxygen deficiency and semiconducting properties. The oxygen deficiency in metal-oxide layer 104 easily becomes an active site of the oxygen reduction reaction. In other words, metal-oxide layer 104 easily reacts with hydrogen. Gas sensor 100A can, therefore, be realized with reaction characteristics in respect with a stable hydrogen.

First electrode 103 and second electrode 105 may include, for example, platinum (Pt), iridium (Ir), palladium (Pd), silver (Ag), Ni, W, Cu, Al, Ta, Ti, titanium nitride (TiN), tantalum nitride (TaN), and titanium aluminum nitride (TiAlN).

Concretely, second electrode 105 includes a material having a catalytic action in which hydrogen atoms are dissociated from gas molecules with hydrogen atoms, e.g. Pt, Ir, Pd, or an alloy including at least one of these.

First electrode 103 may include a material with a lower standard electrode potential than a metal including a metal oxide, e.g. W, Ni, Ta, Ti, Al, TaN, and TiN. The standard electrode potential oxidizes less easily as this value increases.

First electrode 103 includes a material having a catalytic action in which hydrogen atoms are dissociated from gas molecules with hydrogen atoms, e.g. Pt, Ir, Pd, or an alloy including at least one of these, similar to second electrode 105.

Substrate 101 can be, for example, a monocrystalline silicon substrate or a semiconductor substrate, but is not limited hereto. Since metal-oxide layer 104 can be formed at a comparatively low substrate temperature, metal-oxide layer 104 can also, for example, be formed on a resin.

Embodiment 3

Adopting the hydrogen detection apparatus in a fuel cell vehicle will be described in Embodiment 3. A hydrogen detection apparatus according to Embodiment 3 is installed in the fuel cell vehicle, and monitors for hydrogen leaks in the fuel cell vehicle.

(Configuration of Fuel Cell Vehicle)

Figures 6, 7A, 7B:
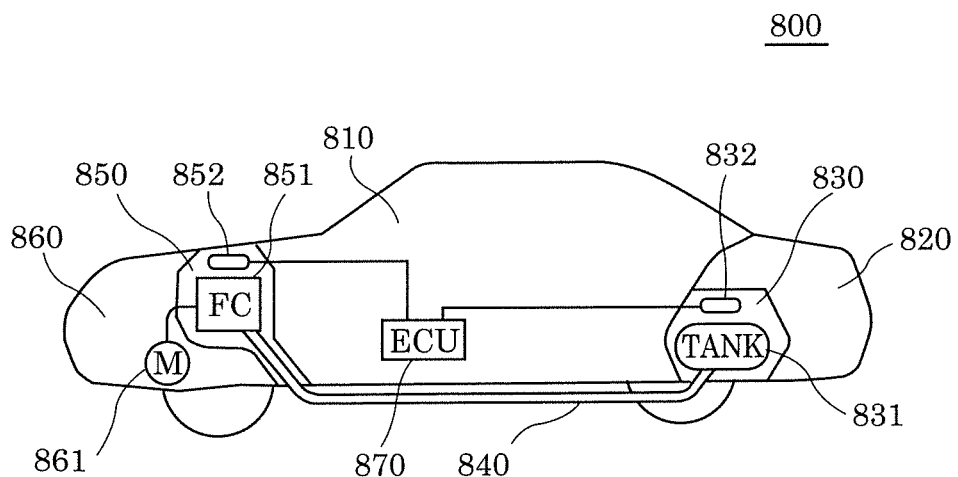
FIG. 6 is a schematic view of an example of a configuration of a fuel cell vehicle according to Embodiment 3.
FIG. 7A is a diagram showing an example of an off time table according to Embodiment 3.
FIG. 7B is a diagram showing an example of an off time table according to Embodiment 3.

FIG. 6 is a schematic view of an example of a configuration of fuel cell vehicle 800 according to Embodiment 3.

Fuel cell vehicle 800 includes passenger compartment 810, luggage compartment 820, gas tank compartment 830, fuel tank 831, hydrogen detection apparatus 832, pipe 840, fuel cell compartment 850, fuel cell 851, hydrogen detection apparatus 852, motor compartment 860, motor 861, and electronic control unit (ECU) 870.

Fuel tank 831 is disposed inside gas tank compartment 830, and retains hydrogen gas as fuel gas. Hydrogen detection apparatus 832 detects fuel gas leaks in gas tank compartment 830.

Fuel cell 851 includes a fuel cell stack that contains a plurality of cell stacked on top of one another and that uses fuel electrodes, air electrodes, and electrolytes as the main units thereof. Fuel cell 851 is disposed in fuel cell compartment 850. Hydrogen gas inside fuel tank 831 passes through pipe 840 and is fed to fuel cell 851 in fuel cell compart- 850. Power is generated by causing this hydrogen gas and oxygen gas in the air to react inside fuel cell 851. Hydrogen detection apparatus 852 detects fuel gas leaks in gas tank compartment 850.

Motor 861 is disposed in motor compartment 860. Fuel cell vehicle 800 is caused to travel due to a rotation of motor 861 using the electric power generated by fuel cell 851.

ECU 870 performs the overall control of fuel cell vehicle 800, e.g. (i) control of the power generation in fuel cell 851, (ii) torque control of motor 861, (iii) detection of various operations by a driver, e.g. steering, accelerating, breaking, and gear shifting, (iv) and detection of a speed and acceleration of fuel cell vehicle 800.

(Hydrogen Detection Operation in Fuel Cell Vehicle)

For example, hydrogen detection apparatus 1 as described in Embodiment 1 is used in hydrogen detection apparatuses 832 and 852 in fuel cell vehicle 800. The hydrogen detection by hydrogen detection apparatuses 832 and 852 is performed as follows.

ECU 870 supplies a state signal indicating the parked, stopped, and traveling states of fuel cell vehicle 800 to hydrogen detection apparatuses 832 and 852 based on the detecting operations of the driver, the speed of fuel cell vehicle 800, and the like. The parked, stopped, and traveling states of fuel cell vehicle 800 are each an example of the operating environment of hydrogen detection apparatuses 832 and 852.

Hydrogen detection apparatuses 832 and 852 set an off time that differs depending on a state of fuel cell vehicle 800 displayed in the state signal supplied from ECU 870, and intermittently perform the hydrogen detection operation.

FIG. 7A is a diagram showing an example of an off time table used by hydrogen detection apparatuses 832 and 852.

In the example of FIG. 7A, microcomputer 300 sets an off time when fuel cell vehicle 800 is driving as t3, and an off time when fuel cell vehicle 800 is parked as t1 that is longer than t3. Microcomputer 300 sets an off time when fuel cell vehicle 800 is driving as t3, and an off time when fuel cell vehicle 800 is stopped as t2 that is longer than t3.

This makes it possible, in the traveling state in which hydrogen gas is actually transferred and consumed in fuel cell vehicle 800, to reliably ensure the safety of fuel cell vehicle 800 by frequently monitoring for hydrogen leaks using the shorter off time t3. In the parked state in which the transferring and consumption of hydrogen gas is completely stopped, and the stopped state in which these are mostly stopped, power consumption is reduced while ensuring the safety of fuel cell vehicle 800, and hydrogen detection apparatuses 832 and 852 can save more energy by reducing the monitoring frequency for hydrogen leaks using the longer off times t1 and t2.

FIG. 7B is a diagram showing another example of an off time table used by hydrogen detection apparatuses 832 and 852. The off time table in FIG. 7B differs with the off time table in FIG. 7A in that the off time is divided into whether fuel cell vehicle 800 is parked in an enclosed space or whether fuel cell vehicle 800 is parked in an open space.

Enclosed space here means a space in which hydrogen gas can readily be refilled, and may include, for example, a built-in garage of a residence, an indoor parking area of a public facility, and a tower parking facility. Open space here means a space in which hydrogen gas cannot readily be refilled, and may include, for example, a carport of a residence, an outdoor parking area of a public facility, and a rooftop parking area. Whether the parking space is an enclosed space or an open space may be notified through a wireless signal by the parking facility.

In the example of FIG. 7B, microcomputer 300 sets an off time when fuel cell vehicle 800 is parked in an enclosed space as t1$b$ that is longer than t3, and an off time when fuel cell vehicle 800 is parked in an open space as t1$a$ that is longer than t1$b$.

This makes it possible to optimizing the trade-off between ensuring the safety of fuel cell vehicle 800 and saving energy by setting the monitoring frequency for hydrogen leaks in the parked state in accordance with how easily hydrogen gas can be refilled when a hydrogen leak has occurred in the parking space.

Embodiment 4

Adopting a pipeline of the hydrogen detection apparatus for transporting hydrogen gas (hereinafter, referred in short as hydrogen pipeline) will be described in Embodiment 4. A hydrogen detection apparatus according to Embodiment 4 is disposed in the hydrogen pipeline and monitors for hydrogen leaks therein.

(Configuration of Hydrogen Leak Monitoring System)

Figure 8:
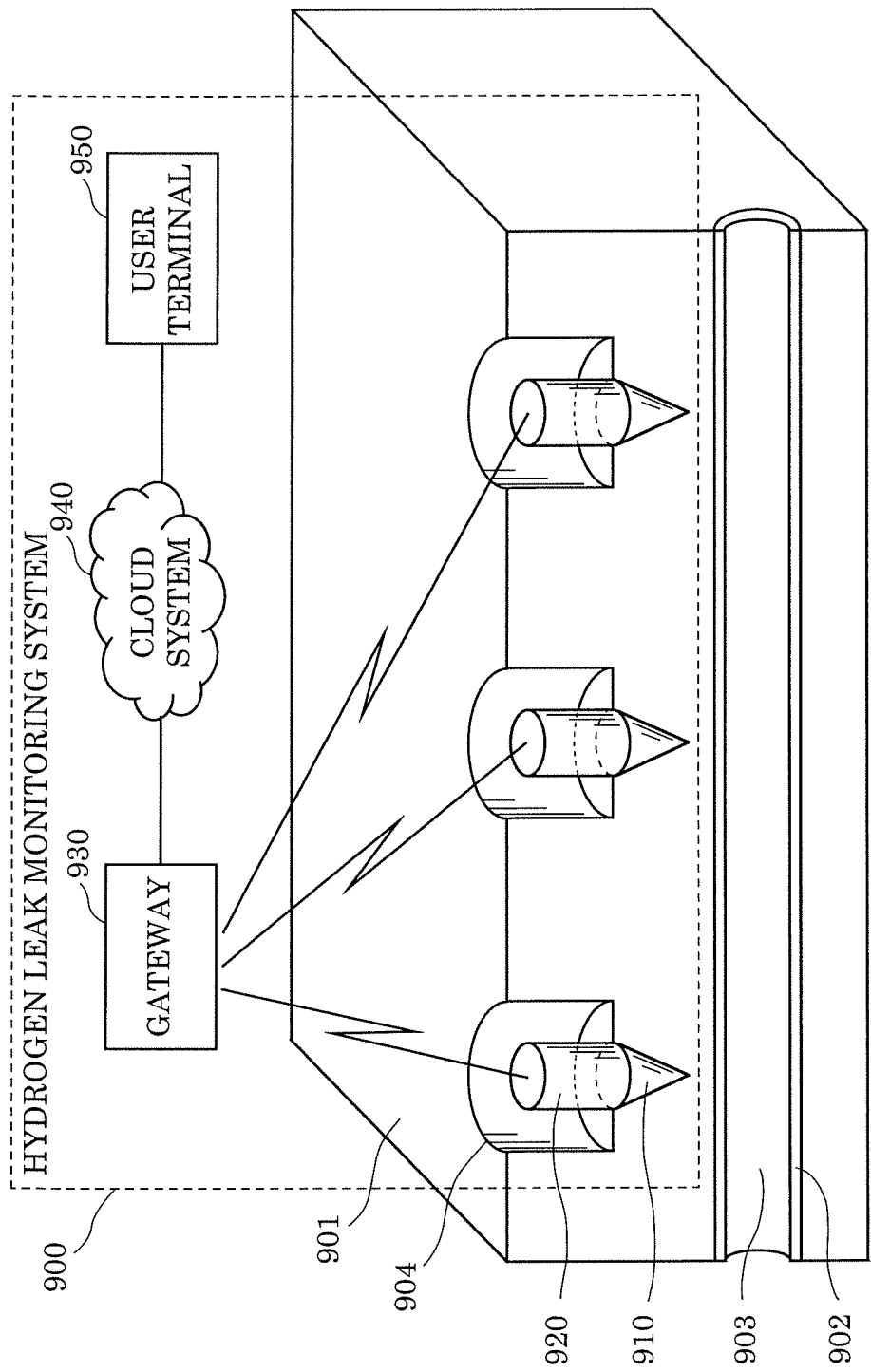
FIG. 8 is a schematic view of an example of a configuration of a hydrogen leak monitoring system according to Embodiment 4.

FIG. 8 is a schematic view of an example of a configuration of hydrogen leak monitoring system 900 according to Embodiment 4.

Hydrogen leak monitoring system 900 includes compound sensor module 910, communication module 920, gateway 930, cloud system 940, and user terminal 950.

Compound sensor module 910 includes, for example, a sensor that detects at least one of a temperature, humidity, oscillation, pressure, and submersion of a monitoring target (here, the hydrogen pipeline), along with hydrogen detection apparatus 1 described in Embodiment 1. Compound sensor module 910 (especially the hydrogen sensor included in compound sensor module 910) is disposed above hydrogen transport pipe 902 for transporting hydrogen gas 903.

Communication module 920 transmits a detection signal indicating a hydrogen detection result provided by compound sensor module 910.

Gateway 930 receives the detection signal from communication module 920 and forwards the received detection signal to cloud system 940.

Cloud system 940 is a network computer system connecting a server apparatus to a network, receives the detection signal with the server apparatus via the network, and aggregates the hydrogen detection results provided by compound sensor module 910 in the server apparatus.

User terminal 950 provides a user interface of hydrogen leak monitoring system 900. To be specific, a warning from compound sensor module 910 indicating that hydrogen has been detected is sent to an operator using sound, light, vibration, and the like.

In the example of FIG. 8, hydrogen transport pipe 902 is buried under ground 901, and compound sensor module 910 and communication module 920 are disposed inside handhole 904 that is disposed in ground 901, but these are not limited to this example. For example, hydrogen transport pipe 902 may also be laid throughout a hydrogen-related facility. Compound sensor module 910 may also be disposed, for example, at each seam of hydrogen transport pipe 902 (not illustrated).

(Configuration of Compound Sensor Module)

A configuration of compound sensor module 910 will be described next.

Figures 9, 10:
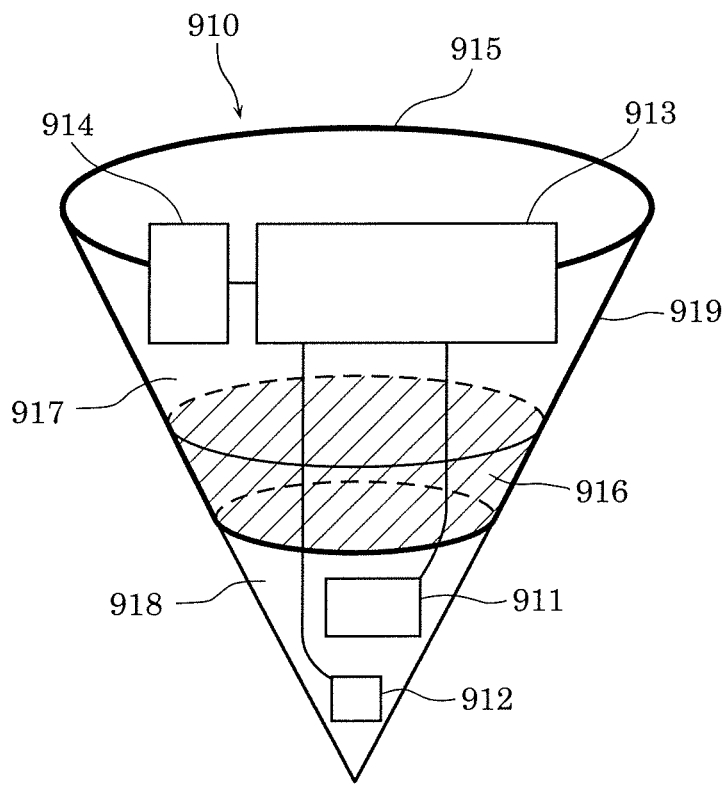
FIG. 9 is a schematic view of an example of a configuration of a compound sensor module according to Embodiment 4.
FIG. 10 is a diagram showing an example of an off time table according to Embodiment 4.

FIG. 9 is a schematic view of an example of a configuration of compound sensor module 910. As illustrated in FIG. 9, compound sensor module 910 includes a cone-shaped housing 915 that houses environment sensor 911 including the hydrogen sensor, control circuit 913, and power source 914. One compound sensor module 910 may further include submersion sensor 912 as a part of environment sensor 911.

Housing 915 is divided into first compartment 917 and second compartment 918 by a waterproof and dustproof filter 916. First compartment 917 includes control circuit 913 and power source 914. An inside of first compartment 917 is protected from water and dust by coating material 919 and filter 916 applied to a surface of housing 915. Second compartment 918 includes environment sensor 911. An inside of second compartment 918 communicates with an exterior of housing 915 so that at least hydrogen gas can enter. When compound sensor module 910 includes submersion sensor 912, submersion sensor 912 is disposed under environment sensor 911 inside second compartment 918.

Environment sensor 911 includes at least the hydrogen sensor, and may further a sensor that detects at least one of a temperature, humidity, oscillation, pressure, and submersion of an installation environment (here, the hydrogen pipeline). The hydrogen sensor included in environment sensor 911 may also be hydrogen sensor 100 in hydrogen detection apparatus 1 described in Embodiment 1. Submersion sensor 912 is an example of environment sensor 911 that detects the submersion of compound sensor module 910.

Control circuit 913 intermittently drives environment sensor 911 (including the hydrogen sensor), and may include sensor control circuit 200 and microcomputer 300 of hydrogen detection apparatus 1 described in Embodiment 1.

Power source 914 includes a battery and power source circuit not illustrated in the drawings, and supplies operating power to all sensor modules 910.

(Hydrogen Detection Operation in Hydrogen Leak Monitoring System)

The hydrogen detection of compound sensor module 910 in hydrogen leak monitoring system 900 is performed as follows.

Control circuit 913 in compound sensor module 910 measures at least one of a temperature, humidity, oscillation, and pressure using environment sensor 911, and determines fuel cell vehicle 800 to be in a normal state when a measured value is within a preset control range, and a caution state when the measured value is outside the control range. Control circuit 913 may determine fuel cell vehicle 800 to be in a malfunction state in which correct hydrogen detection cannot be performed when submersion sensor 912 is provided and a submersion has been detected.

Control circuit 913 sets an off time that differs depending on the detected state, and intermittently performs the hydrogen detection operation.

FIG. 10 is a diagram of an example of an off time table used by compound sensor module 910.

In the example of FIG. 10, microcomputer 300 sets an off time during a caution state as t5, and an off time during a normal state as t4 that is longer than t5.

This makes it possible to more reliably ensure the safety of fuel cell vehicle 800 by increasing the monitoring frequency for hydrogen leaks since a risk of hydrogen leaks is believed to be higher in the caution state in which an anomalous value has been detected concerning at least one of a temperature, humidity, oscillation, and pressure of the hydrogen pipeline. Power consumption can be reduced while ensuring the safety of fuel cell vehicle 800 and compound sensor module 910 can save more energy by decreasing the monitoring frequency for hydrogen leaks in the normal state in which the anomalous value is not detected.

In the malfunction state in which submersion has been detected, the off time is set to an indefinite duration and the hydrogen detection is suspended.

This makes it possible to increase the reliability of fuel cell vehicle 800 by, for example, reallocating the remaining electric power to a warning of the malfunction state when the correct hydrogen detection cannot be continued.

Variations

A hydrogen detection apparatus, fuel cell vehicle, hydrogen leak monitoring system, compound sensor module, hydrogen detection method, and computer program according to several aspects of the present disclosure have been described above based on the embodiments, but the present disclosure is not limited thereto. Forms obtained by various combinations of the components in each of the embodiments that can be conceived by a person skilled in the art which are within the scope of the essence of the present disclosure may be included in the scope of the one or more aspects of the present disclosure.

Outline of Aspects

A hydrogen detection apparatus according to an aspect includes a hydrogen sensor in which a resistance value fluctuates in response to a presence of a hydrogen gas, a sensor control circuit that senses the resistance value of the hydrogen sensor, and a microcomputer that sets an off time that differs depending on an operating environment and intermittently drives the sensor control circuit. The hydrogen sensor includes a first electrode; a metal-oxide layer that is disposed on the first electrode, and in which a resistance value changes in response to contacting hydrogen atoms; a second electrode disposed on the metal-oxide layer; and an insulating film that covers at least a portion of lateral surfaces of the first electrode, the metal-oxide layer, and the second electrode. A portion of at least one of (i) a first interface between the first electrode and the metal-oxide layer and (ii) a second interface between the second electrode and the metal-oxide layer is uncovered by the insulating film and exposed to a detection space.

Such a configuration makes it possible to use a hydrogen sensor that detects hydrogen gas based on a resistance fluctuation that occurs due to a reduction reaction caused by hydrogen atoms in the metal-oxide layer. The hydrogen atoms that oxidize the metal-oxide layer are dissociated from hydrogen gas in the detection space, and the dissociation to the hydrogen atoms predominantly occurs at the first interface and the second interface. The above configuration in which at least a portion of one of the first interface and the second interface is exposed to the detection space makes it, therefore, possible to attain a hydrogen detection apparatus that is highly capable of detecting hydrogen gas since the hydrogen atoms are efficiently dissociated and the reduction reaction in the metal-oxide layer goes smoothly.

Such a configuration makes it possible to set an off time that differs depending on the operating environment, and intermittently perform the hydrogen detection, i.e., perform the hydrogen detection with a different frequency in accordance with the operating environment. This makes it possible, for example, to optimize the trade-off between ensuring the safety of the hydrogen detection apparatus and saving energy since operations such as shortening an off time and frequently performing the hydrogen detection become possible in environments where there is a high risk of hydrogen leaks compared to environments where there is a low risk of hydrogen leaks.

At least one of the first electrode and the second electrode, having the at least one of the first interface and the second interface with the metal-oxide layer, may include a material having a catalytic action that causes the hydrogen atoms to be dissociated from gas molecules.

Such a configuration makes it possible to efficiently reduce the resistance value between the first electrode and the second electrode due to the hydrogen atoms being dissociated from the gas molecules in the catalytic action and the dissociated hydrogen atoms bonding with the oxygen atoms inside the metal-oxide layer. This makes it possible to attain a hydrogen sensor that is highly capable of detecting hydrogen gas.

The at least one of the first electrode and the second electrode may include platinum, and the metal-oxide layer may include tantalum oxide.

Such a configuration makes it possible to cause the hydrogen atoms to be dissociated efficiently in the catalytic action of the platinum, and to attain a hydrogen sensor that is highly capable of detecting gas including hydrogen since the tantalum oxide that is highly capable of changing the resistance is used for the metal-oxide layer.

The hydrogen detection apparatus may be installed in a fuel cell vehicle, and the microcomputer may set an off time that differs depending on a state of the fuel cell vehicle and intermittently drive the sensor control circuit.

Such a configuration makes it possible to attain a hydrogen detection apparatus that can optimize the trade-off between ensuring the safety of the fuel cell vehicle and saving energy since the hydrogen detection can be performed at a suitable frequency based on the risk of hydrogen leaks in accordance with the state of the fuel cell vehicle when the hydrogen detection apparatus is used for monitoring for hydrogen leaks in the fuel cell vehicle.

The microcomputer may set an off time when the fuel cell vehicle is driving as t3, and an off time when the fuel cell vehicle is parked as t1 that is longer than t3.

The microcomputer may set an off time when the fuel cell vehicle is parked in an enclosed space as t1b that is longer than t3, and an off time when the fuel cell vehicle is parked in an open space as t1a that is longer than t1b.

The microcomputer may set an off time when the fuel cell vehicle is driving as t3, and an off time when the fuel cell vehicle is parked as t2 that is longer than t3.

These configurations make it possible to optimize the trade-off between ensuring the safety of the fuel cell vehicle and saving energy since the hydrogen detection can be performed at a suitable frequency based on a substantial risk of foreseen hydrogen leaks in accordance with the state of the fuel cell vehicle.

The hydrogen detection apparatus may be disposed in a pipeline for transporting the hydrogen gas, and the microcomputer may set an off time that differs depending on a state of the pipeline and intermittently drive the sensor control circuit.

Such a configuration makes it possible to attain a hydrogen detection apparatus that can optimize the trade-off between ensuring the safety of the fuel cell vehicle and saving energy since the hydrogen detection can be performed at a suitable frequency based on the risk of hydrogen leaks in accordance with the state of the pipeline when the hydrogen detection apparatus is used for monitoring for hydrogen leaks in the pipeline.

The microcomputer may set an off time when an anomaly in at least one of a temperature, a humidity, an oscillation, and a pressure is detected in the pipeline as t5, and an off time when an anomaly is not detected as t4 that is longer than t5.

This configuration makes it possible to optimize the trade-off between ensuring the safety of the fuel cell vehicle and saving energy since the hydrogen detection can be performed at a suitable frequency based on a substantial risk of foreseen hydrogen leaks in accordance with the state of the pipeline.

A fuel cell vehicle according to a disclosed aspect includes a passenger compartment, a gas tank compartment including a tank of the hydrogen gas, a fuel cell compartment including a fuel cell, and the hydrogen detection apparatus. The hydrogen sensor of the hydrogen detection apparatus is disposed in at least one of the gas tank compartment and the fuel cell compartment.

Such a configuration makes it possible to optimize the trade-off between ensuring the safety of the fuel cell vehicle and saving energy when the hydrogen detection apparatus is monitoring for hydrogen leaks in the fuel cell vehicle.

A hydrogen leak monitoring system according to a disclosed aspect includes the hydrogen detection apparatus; a wireless module that is connected to the hydrogen detection apparatus, and transmits a signal indicating a hydrogen detection result provided by the hydrogen detection apparatus; and a user terminal that obtains the signal, and presents to a user the hydrogen detection result indicated in the signal. A hydrogen sensor of the hydrogen detection apparatus is disposed in an upper part of a hydrogen transport pipe.

Such a configuration makes it possible to optimize the trade-off between ensuring the safety of the fuel cell vehicle and saving energy when the hydrogen detection apparatus is monitoring for hydrogen leaks in the pipeline for transporting hydrogen gas.

A compound sensor module according to a disclosed aspect includes the hydrogen detection apparatus; an environmental sensor that detects at least one of a temperature, a humidity, an oscillation, a pressure, and submersion; and a power source that supplies operating power to the hydrogen detection apparatus and the environmental sensor. The microcomputer changes an off time in the hydrogen detection apparatus in accordance with a detection result of the environmental sensor.

Such a configuration makes it possible to attain a highly user-friendly compound module that can autonomously detect environmental factors related to a risk of hydrogen leaks, and determine an off time for intermittently monitoring for hydrogen leaks.

A hydrogen detection method according to a disclosed aspect uses a hydrogen sensor in which a resistance value fluctuates in response to a presence of a hydrogen gas. The hydrogen sensor includes a first electrode; a metal-oxide layer that is disposed on the first electrode, and in which a resistance value changes in response to contacting hydrogen atoms; a second electrode disposed on the metal-oxide layer; and an insulating film that covers at least a portion of lateral surfaces of the first electrode, the metal-oxide layer, and the second electrode. A portion of at least one of (i) a first interface between the first electrode and the metal-oxide layer and (ii) a second interface between the second electrode and the metal-oxide layer is uncovered by the insulating film and exposed to a detection space. The hydrogen detection method includes (i) setting an off time that differs depending on an operating environment, and (ii) setting the off time, and intermittently driving a sensor control circuit that senses the resistance value of the hydrogen sensor.

Such a method makes it possible to set an off time that differs depending on the operating environment, and intermittently perform the hydrogen detection, i.e., perform the hydrogen detection with a different frequency in accordance with the operating environment. This makes it possible, for example, to attain a hydrogen detection method that can optimize the trade-off between ensuring the safety of the hydrogen detection apparatus and saving energy since operations such as shortening an off time and frequently performing the hydrogen detection become possible in environments where there is a high risk of hydrogen leaks compared to environments where there is a low risk of hydrogen leaks.

A non-transitory computer-readable recording medium having stored thereon a computer program for causing a microcomputer to execute a hydrogen detection using a hydrogen sensor in which a resistance value fluctuates in response to a presence of a hydrogen gas. The hydrogen sensor includes a first electrode; a metal-oxide layer that is disposed on the first electrode, and in which a resistance value changes in response to contacting hydrogen atoms; a second electrode disposed on the metal-oxide layer; and an insulating film that covers at least a portion of lateral surfaces of the first electrode, the metal-oxide layer, and the second electrode. A portion of at least one of (i) a first interface between the first electrode and the metal-oxide layer and (ii) a second interface between the second electrode and the metal-oxide layer is uncovered by the insulating film and exposed to a detection space. The recording medium includes (i) setting an off time that differs depending on an operating environment, and (ii) setting the off time, and intermittently driving a sensor control circuit that senses the resistance value of the hydrogen sensor.

Such a configuration makes it possible to attain a non-transitory computer-readable recording medium having stored thereon a computer program for executing the hydrogen detection method that can optimize the trade-off between ensuring the safety of the hydrogen detection apparatus and saving energy.

INDUSTRIAL APPLICABILITY

A hydrogen detection apparatus according to the present disclosure can be widely used in hydrogen-related facilities, e.g. hydrogen pipelines, fuel cell vehicles, hydrogen stations, and hydrogen plants.

The invention claimed is:
1. A hydrogen detection apparatus, comprising:
a hydrogen sensor in which a resistance value is configured to fluctuate in response to a presence of a hydrogen gas;
a sensor control circuit configured to sense the resistance value of the hydrogen sensor; and
a microcomputer configured to set an off time that differs depending on an operating environment, and intermittently drive the sensor control circuit,
wherein the hydrogen sensor includes:
a first electrode;
a metal-oxide layer that is disposed on the first electrode, and in which a resistance value is configured to change in response to contacting hydrogen atoms;
a second electrode disposed on the metal-oxide layer and the first electrode such that the metal-oxide layer is sandwiched in between the first electrode and the second electrode in a thickness direction of the hydrogen sensor; and
an insulating film that covers at least a portion of lateral surfaces of the first electrode, the metal-oxide layer, and the second electrode, and
wherein a portion of at least one of: (i) a first interface between the first electrode and the metal-oxide layer; and (ii) a second interface between the second electrode and the metal-oxide layer is uncovered by the insulating film and exposed to a detection space.

2. The hydrogen detection apparatus according to claim 1, wherein
at least one of the first electrode and the second electrode, having the at least one of the first interface with the metal-oxide layer and the second interface with the metal-oxide layer, includes a material having a catalytic action configured to cause the hydrogen atoms to be dissociated from gas molecules.

3. The hydrogen detection apparatus according to claim 2, wherein:
the at least one of the first electrode and the second electrode includes platinum; and
the metal-oxide layer includes tantalum oxide.

4. A fuel cell vehicle, comprising:
the hydrogen detection apparatus according to claim 1,
wherein the operating environment is a state of the fuel cell vehicle.

5. The fuel cell vehicle according to claim 4, wherein
the microcomputer is configured to set the off time when the fuel cell vehicle is driving as t3, and the off time when the fuel cell vehicle is parked as t1 that is longer than t3.

6. The fuel cell vehicle according to claim 5, wherein
the microcomputer is configured to set the off time when the fuel cell vehicle is parked in an enclosed space as t1$b$ that is longer than t3, and the off time when the fuel cell vehicle is parked in an open space as t1$a$ that is longer than t1$b$.

7. The fuel cell vehicle according to claim 4, wherein
the microcomputer is configured to set the off time when the fuel cell vehicle is driving as t3, and the off time when the fuel cell vehicle is stopped as t2 that is longer than t3.

8. A pipeline for transporting hydrogen gas, the pipeline comprising:
the hydrogen detection apparatus according to claim 1,
wherein the operating environment is a state of the pipeline.

9. The pipeline according to claim 8, wherein
the microcomputer is configured to set the off time when an anomaly in at least one of a temperature, a humidity, an oscillation, and a pressure is detected in the pipeline as t5, and the off time when an anomaly is not detected as t4 that is longer than t5.

10. The fuel cell vehicle of claim 4, further comprising:
a passenger compartment;
a gas tank compartment including a tank of the hydrogen gas; and
a fuel cell compartment including a fuel cell,
wherein the hydrogen sensor of the hydrogen detection apparatus is disposed in at least one of the gas tank compartment and the fuel cell compartment.

11. A hydrogen leak monitoring system, comprising:
the pipeline according to claim 8,
a communication module that is connected to the hydrogen detection apparatus, and configured to transmit a signal indicating a hydrogen detection result provided by the hydrogen detection apparatus; and a user terminal configured to obtain the signal, and present to a user the hydrogen detection result indicated in the signal, wherein the hydrogen sensor of the hydrogen detection apparatus is disposed in an upper part of a hydrogen transport pipe.

12. A compound sensor module, comprising:

the hydrogen detection apparatus according to claim 1;

an environmental sensor configured to detect at least one of a temperature, a humidity, an oscillation, a pressure, and a submersion; and a power source configured to supply operating power to the hydrogen detection apparatus and the environmental sensor, wherein the microcomputer is configured to change the off time in the hydrogen detection apparatus in accordance with a detection result of the environmental sensor.

13. A hydrogen detection method using a hydrogen sensor in which a resistance value fluctuates in response to a presence of a hydrogen gas, wherein the hydrogen sensor includes:

a first electrode;

a metal-oxide layer that is disposed on the first electrode, and in which a resistance value changes in response to contacting hydrogen atoms;

a second electrode disposed on the metal-oxide layer and the first electrode such that the metal-oxide layer is sandwiched in between the first electrode and the second electrode in a thickness direction of the hydrogen sensor; and an insulating film that covers at least a portion of lateral surfaces of the first electrode, the metal-oxide layer, and the second electrode, wherein a portion of at least one of: (i) a first interface between the first electrode and the metal-oxide layer; and (ii) a second interface between the second electrode and the metal-oxide layer is uncovered by the insulating film and exposed to a detection space, and wherein the hydrogen detection method comprises:

setting an off time that differs depending on an operating environment; and setting the off time, and intermittently driving a sensor control circuit that senses the resistance value of the hydrogen sensor.

14. A non-transitory computer-readable recording medium having stored thereon a computer program for causing a microcomputer to execute a hydrogen detection method using a hydrogen sensor in which a resistance value fluctuates in response to a presence of a hydrogen gas, wherein the hydrogen sensor includes:

a first electrode;

a metal-oxide layer that is disposed on the first electrode, and in which a resistance value changes in response to contacting hydrogen atoms;

a second electrode disposed on the metal-oxide layer and the first electrode such that the metal-oxide layer is sandwiched in between the first electrode and the second electrode in a thickness direction of the hydrogen sensor; and an insulating film that covers at least a portion of lateral surfaces of the first electrode, the metal-oxide layer, and the second electrode, wherein a portion of at least one of: (i) a first interface between the first electrode and the metal-oxide layer; and (ii) a second interface between the second electrode and the metal-oxide layer is uncovered by the insulating film and exposed to a detection space, and wherein the hydrogen detection method comprises:

setting an off time that differs depending on an operating environment; and setting the off time, and intermittently driving a sensor control circuit that senses the resistance value of the hydrogen sensor.

\* \* \* \* \*